(12) United States Patent
Vandamme

(10) Patent No.: US 9,719,899 B2
(45) Date of Patent: Aug. 1, 2017

(54) TEST METHOD FOR AGRICULTURAL BALER

(71) Applicant: CNH Industrial America LLC, New Holland, PA (US)

(72) Inventor: Dirk A. R. Vandamme, Uitkerke (BE)

(73) Assignee: CNH Industrial America LLC, New Holland, PA (US)

( * ) Notice: Subject to any disclaimer, the term of this patent is extended or adjusted under 35 U.S.C. 154(b) by 265 days.

(21) Appl. No.: 14/535,681

(22) Filed: Nov. 7, 2014

(65) Prior Publication Data

US 2015/0128718 A1     May 14, 2015

(30) Foreign Application Priority Data

Nov. 8, 2013  (BE) .................................. 2013/0760

(51) Int. Cl.
| | |
|---|---|
| *G01L 25/00* | (2006.01) |
| *G01N 3/08* | (2006.01) |
| *A01F 15/04* | (2006.01) |
| *A01F 15/08* | (2006.01) |

(52) U.S. Cl.
CPC ................ *G01N 3/08* (2013.01); *A01F 15/04* (2013.01); *A01F 15/08* (2013.01); *G01L 25/00* (2013.01)

(58) Field of Classification Search
CPC ........ A01F 15/08; A01F 15/04; A01F 15/044; B30B 9/3007; G01M 13/00; G01M 99/005; G01L 5/0061; G01L 5/0066; G01L 25/00

See application file for complete search history.

(56) References Cited

U.S. PATENT DOCUMENTS

| | | |
|---|---|---|
| 5,226,356 A | 7/1993 | Schrag et al. |
| 6,101,932 A | 8/2000 | Wilkens |
| 6,248,963 B1 * | 6/2001 | Gottlober ............ A01F 15/0825 177/136 |
| 6,457,405 B1 | 10/2002 | Lippens et al. |
| 7,007,599 B2 | 3/2006 | Roth |
| 7,174,831 B2 | 2/2007 | Roth |
| 2014/0202343 A1 | 7/2014 | Van Amstel et al. |

FOREIGN PATENT DOCUMENTS

| | | |
|---|---|---|
| EP | 1516526 A1 | 3/2005 |
| WO | 2013135794 A1 | 9/2013 |

* cited by examiner

*Primary Examiner* — Blake A Tankersley
(74) *Attorney, Agent, or Firm* — Patrick M. Sheldrake

(57) ABSTRACT

A system and method for verifying the operational condition of a rectangular baler having a baling chamber equipped with a reciprocating plunger, the plunger moving between a fully retracted position and extended position, the baler further equipped with a load sensor suitable for determining the reaction force on the plunger as said plunger is compressing crops. Verifying the operational condition includes measuring the reaction force on the plunger or a parameter related to said reaction force, when the plunger is in a position in which it is not exerting a compressive force on the crop material in the baling chamber, comparing the measured reaction force or the parameter to a predefined reference value, and deriving from that comparison an assessment of the baler's condition

9 Claims, 2 Drawing Sheets

TEST METHOD FOR AGRICULTURAL BALER

CROSS REFERENCE TO RELATED APPLICATIONS

This Patent Application claims priority under 35 U.S.C. §119 to BE 2013/0760 filed on Nov. 8, 2013 titled, "Test Method for Agricultural Baler" and having Dirk A. R. Vandamme as the inventor. The full disclosure of BE 2013/0760 is hereby fully incorporated herein by reference.

FIELD OF THE INVENTION

The present invention is related to agricultural balers, used for picking up crop material such as hay or straw from the field or receiving crop material from a harvester, and forming it into rectangular bales.

STATE OF THE ART

Agricultural square or rectangular balers gather crop material into a baling chamber where the material is compressed by a reciprocating plunger to form rectangular bales. When a predetermined amount of crops have been gathered in the baling chamber and compressed by the plunger, a tying mechanism is activated to form a separately tied bale, which is subsequently pushed forward by the continued plunger action.

The compressive force that is exerted by the plunger on the crops in the baling chamber is measured by a load sensor. The measurement can be used to monitor the plunger action and usually also to serve as an input signal for the control of a movable wall of the baling chamber. By movement of the wall, the compressive force can be increased or lowered in response to the load sensor's output signal. EP-A-1066748 shows a sensor arrangement that is in use in many present day balers. Other types of load sensors include strain gauges placed directly on the drive shaft of the plunger mechanism.

Regardless of the type of load sensor that is used, the correct operation of the baler depends on the accuracy of the load measurement. Deviation from a correct load measurement may be due to defects in the sensors themselves or to defects or wear of the baler mechanism as such. In present day machines, a malfunction of the above-described type is difficult to detect, so that suboptimal operation of the baler may go undetected for a prolonged period of time.

SUMMARY OF THE INVENTION

The invention is related to a baler and to a test method for a baler as described in the appended claims. The present invention is related to a method for verifying the operational condition of a rectangular baler used for gathering crop material and forming it into a rectangular bale, the baler comprising a baling chamber equipped with a reciprocating plunger driven by a mechanism comprising a crank shaft and one or more connecting rods, for forming crop material into a rectangular shaped bale, the plunger moving between a fully retracted position and a fully extended position, the baler being further equipped with a load sensor suitable for determining the reaction force on the plunger as said plunger is compressing crops in the baling chamber, the method comprising the steps (performed while running the baler at a given speed of the crank shaft) of measuring the reaction force on the plunger or a parameter related to said reaction force, when the plunger is in a position in which it is not exerting a compressive force on the crop material in the baling chamber, comparing the measured reaction force or the parameter to a predefined reference value, and deriving from that comparison an assessment of the baler's condition. The invention is equally related to a baler equipped with means for performing the method of the invention, to a computer program product which program is operative to cause a processor to perform the method according to the invention, and to a control unit equipped with a means for performing the method.

DETAILED DESCRIPTION OF PREFERRED EMBODIMENTS OF THE INVENTION

Preferred embodiments will now be described with reference to the drawings. The detailed description is not limiting the scope of the invention, which is defined only by the appended claims.

Figure 1:
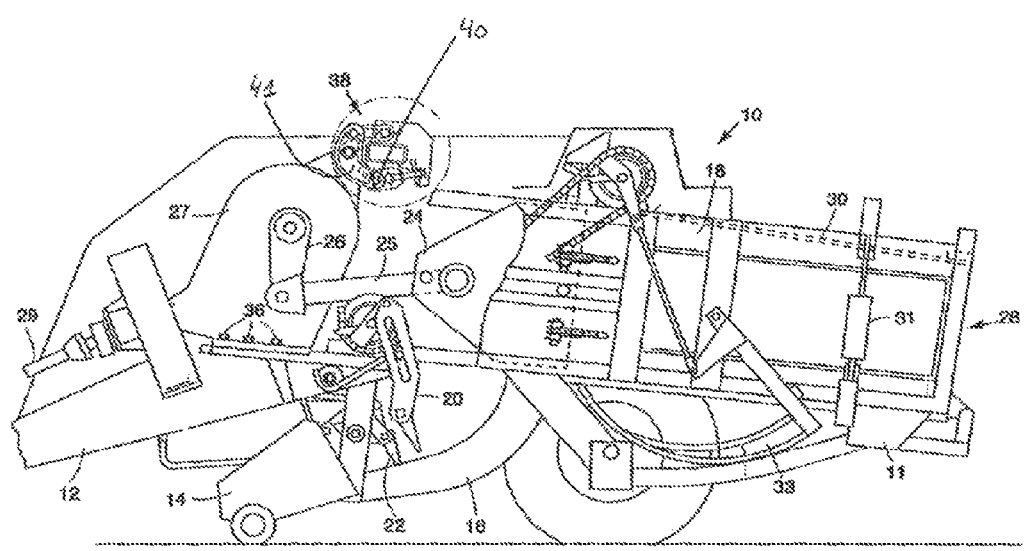
FIG. 1 shows a side view of a baler as known in the art.

FIG. 1 shows the baler described in EP-A-1066748, on the basis of which the invention is explained, even though the invention is not limited to this particular baler. The baler 10 shown in FIG. 1 comprises a main frame 11 which is equipped with a forwardly extending tongue 12 provided at its front end with hitch means (not shown) for coupling the baler 10 to a towing tractor. A pick-up assembly 14 lifts windrowed crop material off the field as the baler 10 is travelled thereover and delivers such material into the front end of a rearwardly and upwardly curved, charge-forming feeder duct 16. The duct 16 communicates at its upper end with an overhead, fore-and-aft extending baling chamber 18 into which crop charges are loaded by a cyclically operating stuffer mechanism 20. A continuously operating packer mechanism 22 at the lower front end of the feeder duct 16 continuously feeds and packs material into the duct 16 as to cause charges of the crop material to take on and assume the internal configuration of the duct 16 prior to periodic engagement by the stuffer 20 and insertion up into the baling chamber 18. Each action of the stuffer 20 introduces a "charge" or "flake" of crop material from the duct 16 into the chamber 18.

A plunger 24 reciprocates in a fore-and-aft direction within the baling chamber 18 under action of a pair of connecting rods 25 (hereafter referred to as 'conrods') which are linked to the crank arms 26 of a gearbox 27 driven by a transmission shaft 29 which is connected to the PTO shaft of the tractor. The reciprocating plunger 24 pushes each new charge introduced into the baling chamber 18 rearwardly and forms the subsequent charges into a parallelepiped package of crop material, which is forced by the same action of the plunger 24 toward a rearmost discharge aperture 28 of the chamber.

The baling chamber 18 comprises at least one movable wall portion 30 of which the position can be adjusted to vary the cross section of the aperture 28. Reduction of this cross section will increase the resistance to rearward movement of the crop packages and hence increase the density of the crop material contained therein. Similarly an enlargement of the cross section will reduce said resistance to rearward movement and hence equally reduce the density of the newly formed packages. The position of the wall portion 30 is controlled by actuator means comprising of a pair of hydraulic cylinders 31 (only one shown in FIG. 1) which are installed between the frame 11 and the wall portion 30.

The gearbox 27 is affixed at its lower section by a set of bolts 36 to the main frame 11. The top portion of the gearbox is held in place by a linkage and sensor assembly 38, comprising a pin-shaped load sensor 40, configured to measure the reaction forces of the crop material on the plunger 24. The sensor is mounted in a mechanism involving a lever 41, configured to minimize the effects of transverse or upward vibrations of the gearbox on the sensor.

The present invention is based on the finding that a particular measurement by the load sensor 40 is representative for the baler's operative condition, i.e. this measurement is capable of giving an indication on whether the baler is operating under the required conditions and is not deteriorated by wear or defects (provided that the sensor itself is not defective). According to a preferred embodiment, this measurement is a measurement by the load sensor at the point in the plunger's movement cycle when the plunger recedes to the fully retracted position, before travelling towards the discharge aperture 28. At this ultimate point, no compression force is applied by the plunger, and the only force registered by the load sensor is the reaction force required to overcome the inertia of the plunger as it comes to a standstill at the fully retracted position of its cycle. This reaction force is an excellent parameter for assessing the baler's operational condition. This measurement can be performed when the baling chamber is empty or while the baling chamber is being filled with crop material, i.e. during normal operation of the baler. In the fully retracted position of the plunger, no compressive force is exerted by the plunger on any crop material in the chamber, whether or not crop material is present in the chamber. According to another embodiment, the measurement by the load sensor is performed when the plunger is in the fully extended position, which is equally a good indicator of the baler's operational condition. However, the latter measurement can only be performed when the baling chamber is empty, as otherwise the reaction force in the fully extended position is mainly determined by the compressive force exerted by the plunger on the crops. In general terms, the measurement of the reactive force on the plunger in the method of the invention can take place at any position of the plunger at which the plunger does not exert a compressive force on the crops. Preferably this is in either the fully retracted or the fully extended position of the plunger, but the measurement could for example be performed a few degrees before or after reaching one of these ultimate points.

The method of the invention thus comprises the following steps, performed while the baler is running at a given speed of the crank shaft 26 (obtained by a given PTO speed and taking into account the speed transmission established by the gearbox 27):

determining the reaction force on the plunger or a parameter related to said reaction force, when the plunger is in a position at which the plunger does not exert a compressive force on crops in the baling chamber, preferably in the fully retracted position and/or the fully extended position of the plunger comparing the measured reaction force or the determined parameter to a predefined reference value, and deriving from that comparison an assessment of the baler's condition.

The reference level may be measured with the plunger reciprocating in an empty baling chamber at a predefined PTO speed, before the baler is first taken into active service. During the lifetime of the baler, the measurement according to the invention, preferably at the same speed as the reference measurement, allows an easy monitoring of the baler's operational condition. Preferably, the method is applied at regular intervals, when the baling chamber is empty, even though as stated, the measurement at or in the vicinity of the fully retracted position can be performed also during normal stuffing operation. According to an embodiment, reference levels could be provided for a plurality of PTO speeds, so that the method can be performed at any one of those speeds, during normal stuffing operation, or during a deliberately applied test procedure, with the baling chamber empty. The method may be performed automatically at start-up or between harvesting runs, and/or during normal operation of the baler.

Figure 2:
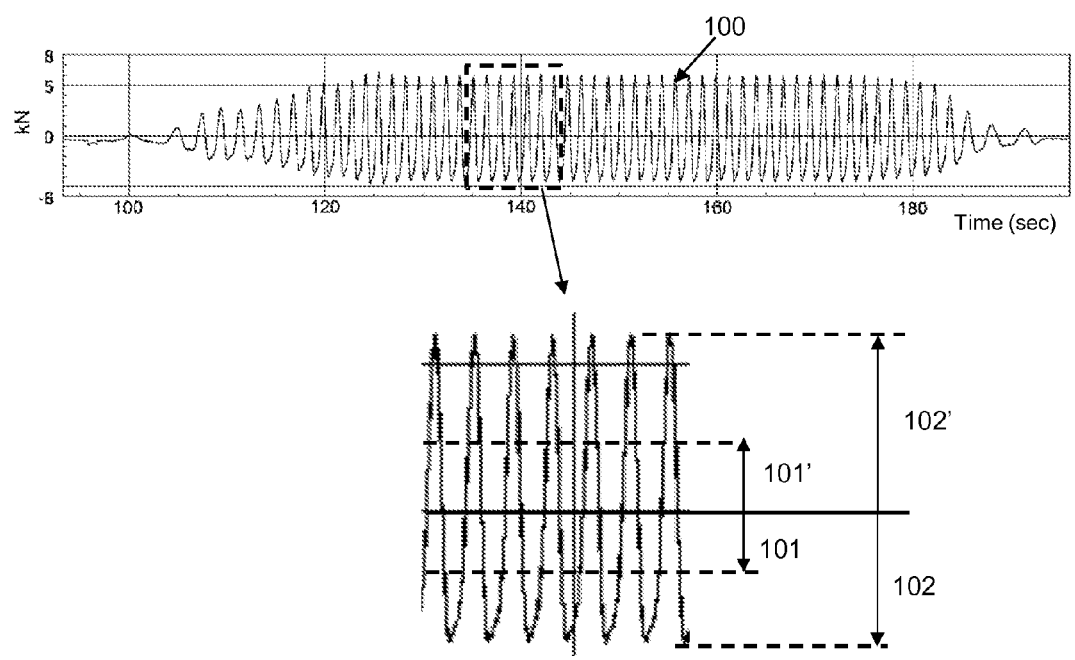
FIG. 2 illustrates the measurements of a load sensor on the basis of which the baler's condition can be tested by applying the method of the invention.

FIG. 2 shows a measurement of the force by the load sensor 40, during a run-up from 0 to 1000 RPM of the PTO speed, while the baling chamber is empty. This translates into a number of reciprocations per minute of the plunger, which are detected by the load sensor in the form of a regular pattern of force peaks 100, extending on either side of the zero load level. The negative peaks correspond to the fully retracted position of the plunger, while the positive peaks correspond to the fully extended position of the plunger. The amplitude of the force peaks is dependent on the PTO speed, and remains constant when the PTO speed is constant at 1000 RPM. The absolute value of the negative or positive peaks represents the reaction force on the plunger when the plunger is in the fully retracted or fully extended position during its reciprocating movement. As stated, this reaction force is a useful parameter for assessing the baler's operational condition. This parameter or any parameter directly related to it can be monitored and compared to a reference level, for example at every startup of the machine, or either continuously or at regular intervals during normal operation. The monitored parameter can for example be the RMS level 101/101' of the negative or positive peaks, the average over a given number of cycles of the absolute values 102/102' of the negative or positive peaks, or similar values derived not from the force curve but from a voltage curve obtained from the output signal of the load sensor. When the monitored parameter deviates more than a given percentage from the reference safety value, the machine can be stopped and inspected. Deviations from the reference can also be due to malfunctions of the load sensor itself. Machine inspection should therefore begin with an inspection or test of the load sensor itself.

The determination of the 'fully retracted' and 'fully extended' positions of the plunger can be based on the force measurement itself, when the force curve is as shown in FIG. 2, i.e. a regular pattern of positive and negative peaks. If however the force profile is less regular due to the appearance of other reaction forces being measured (e.g. due to the movement of the baler as it is driven over a field), it may be required to determine the fully retracted and fully extended position in another way. This may be achieved by utilizing a radial position signal on the crank shaft. Most balers in use today are provided with an encoder on the crank shaft, for determining the crank's position as a function of time. The encoder pulse corresponding to the fully retracted and extended positions can be determined when the baler is first taken into active service, and these pulses can be programmed to trigger the force measurements of the method of the invention. A known reference pulse can for example be used to locate the respective pulses. For example, in some balers there is a known number of crank degrees between the 'reset feeder door pulse' and the fully retracted and extended plunger positions. When the force profile is not a regular pattern as the one shown in FIG. 2, only the absolute value of the measured force or the parameter related to it, is useful as a basis for determining the baler's condition (not an RMS value for example).

The invention is applicable to any type of rectangular baler, equipped with any suitable type of load sensor. For example, instead of the sensor assembly 38 of FIG. 1, the baler may be equipped with strain gauges configured to measure a load profile that is directly linked to the plunger reaction force. Strain gauges applied on the conrods 25 are suitable for this purpose.

The invention is particularly useful when the connecting rods are mounted under a given degree of pretension in the longitudinal direction of the conrods. This may be the case when the conrods are connected to the joint elements of the crank mechanism by bolts which run along the full length of the conrods, to thereby maintain the conrods between constraining elements that are fixed to the crank mechanism's joint element. The use of strain gauges attached to this type of conrods has so far been regarded as unsuitable, given that the pre-tension in the conrods required a careful calibration of the gauges for each machine, in order to set the zero load level. In a baler provided with such gauges on pre-tensioned conrods, and further equipped with the necessary means to perform the method of the invention, this problem is solved: a measurement of the load level with an empty baling chamber can be performed before the machine is taken into active service. The result is a curve as the one shown in FIG. 2, but with the positive peaks not on either side of the zero load level, but on either side of an offset value. This offset value can then be used to reset the zero load level of the strain gauge.

The method of the invention can be brought into practice in the form of a software application that can be incorporated into existing software on board of rectangular balers known in the art. The software may comprise routines for manually executing the method of the invention at any chosen time, during operation of the baler, and/or for automatically executing the method at predefined times during operation, for example before every startup. The invention is thus related to a computer program product which program is operative to cause a processor to perform the method according to the invention, when the program is run on a computer. Such a computer may typically be part of the control unit of a rectangular baler. The invention is therefore related also to such a control unit and to a rectangular baler equipped with such a control unit, or more generally, to a baler equipped with a means for executing the method of the invention, for example equipped with a software application as described above.

The invention claimed is:

1. A method for determining an operational condition of a rectangular agricultural baler, said baler comprising a baling chamber equipped with a reciprocating plunger driven by a mechanism comprising a crank shaft and at least one connecting rod, the plunger moving between a fully retracted position and a fully extended position, the baler being further equipped with a load sensor suitable for determining the reaction force on the plunger as said plunger is compressing crops in the baling chamber, the method comprising the following steps:
   measuring the reaction force on the plunger or a parameter related to said reaction force, when the plunger is in a position in which it is not exerting a compressive force on the crop material in the baling chamber,
   comparing the measured reaction force or the parameter to a predefined reference value, and
   deriving from the compared measured reaction force or parameter an assessment of the operational condition;
   wherein said measuring step is performed when the plunger is in the fully retracted position.

2. Method according to claim 1, wherein the steps are performed when the baling chamber is empty.

3. Method according to claim 1, wherein the steps are performed while the baling chamber is at least partially filled with crop material.

4. Method according to claim 2, wherein the measuring step is performed when the plunger is in the fully extended position.

5. Method according to claim 1, wherein the method steps are automatically performed using a control unit.

6. Method according to claim 1, wherein the load sensor is a pin-shaped load sensor, mounted in a mechanism involving a lever, configured to minimize the effects of transverse or upward vibrations of a gearbox on the sensor.

7. A method for determining an operational condition of a rectangular agricultural baler, said baler comprising a baling chamber equipped with a reciprocating plunger driven by a mechanism comprising a crank shaft and at least one connecting rod, the plunger moving between a fully retracted position and a fully extended position, the baler being further equipped with a load sensor suitable for determining the reaction force on the plunger as said plunger is compressing crops in the baling chamber, the method comprising the following steps:
   measuring the reaction force on the plunger or a parameter related to said reaction force, when the plunger is in a position in which it is not exerting a compressive force on the crop material in the baling chamber,
   comparing the measured reaction force or the parameter to a predefined reference value, and
   deriving from the compared measured reaction force or parameter an assessment of the operational condition;
   wherein the method is performed at multiple plunger speeds of the baler, and wherein multiple predefined reference values are applied corresponding to the multiple speeds.

8. A rectangular agricultural baler comprising:
   a baling chamber equipped with a reciprocating plunger driven by a mechanism comprising a crank shaft and one or more connecting rod connected to the plunger, the plunger moveable between a fully retracted position and a fully extended position,
   a load sensor suitable for determining the reaction force on the plunger as said plunger is compressing crops in the chamber,
   a control system configured to measure the reaction force on the plunger or a parameter related to said reaction force, when the plunger is in the fully retracted or the fully extended position, compare the measured reaction force or the parameter to a predefined reference value determined from a previously measured force by the load sensor and derive from the compared measured reaction force or parameter an assessment of an operational condition,
   wherein the assessment of the operational condition is a determination of the presence of defects or wear related to at least one of the load sensor, the baling chamber, the plunger, and the driving mechanism of the plunger.

9. A control system for a rectangular baler, said baler comprising a baling chamber equipped with a reciprocating plunger driven by a mechanism comprising a crank shaft and one or more connecting rods, for forming crop material into a rectangular shaped bale, the plunger moving between a fully retracted position and a fully extended position, the baler being further equipped with a load sensor suitable for determining the reaction force on the plunger as said plunger is compressing crops in the baling chamber, the control system comprising:

a control unit configured to:
measure the reaction force on the plunger or a parameter related to said reaction force while the baler is running at a given speed of the crank shaft, when the plunger is in a position in which it is not exerting a compressive force on the crop material in the baling chamber,
select a predefined reference value based on the plunger speed of the baler,
compare the measured reaction force or the parameter to the selected predefined reference value, and
derive from the compared measured reaction force or parameter an assessment of an operational condition.

* * * * *